(12) United States Patent
Garcia Gomez

(10) Patent No.: US 7,647,819 B2
(45) Date of Patent: Jan. 19, 2010

(54) APPARATUS FOR TESTING A RUPTURE STRENGTH OF A PIPE

(75) Inventor: Rafael Garcia Gomez, Paderborn (DE)

(73) Assignee: Benteler Automobiltechnik GmbH, Paderborn (DE)

( * ) Notice: Subject to any disclaimer, the term of this patent is extended or adjusted under 35 U.S.C. 154(b) by 363 days.

(21) Appl. No.: 11/614,530

(22) Filed: Dec. 21, 2006

(65) Prior Publication Data

US 2007/0157707 A1 Jul. 12, 2007

(30) Foreign Application Priority Data

Jan. 10, 2006 (DE) .................. 10 2006 001 425

(51) Int. Cl.
*G01M 3/08* (2006.01)
(52) U.S. Cl. .................................... 73/49.1
(58) Field of Classification Search ............ 73/37, 73/40, 46, 49.5, 49.8
See application file for complete search history.

(56) References Cited

U.S. PATENT DOCUMENTS

| | | | | |
|---|---|---|---|---|
| 4,382,379 A | * | 5/1983 | Kelly | .......................... 73/46 |
| 4,770,207 A | * | 9/1988 | Hofmann | .................. 137/557 |
| 6,253,599 B1 | * | 7/2001 | Chang et al. | ............... 73/49.8 |

FOREIGN PATENT DOCUMENTS

| | | |
|---|---|---|
| DE | 2 308 123 A1 | 10/1973 |
| DE | 24 41 358 A1 | 3/1976 |
| DE | 103 56 143 A1 | 6/2005 |
| JP | 62017637 A | 1/1987 |
| WO | WO 97/37206 | 10/1997 |

* cited by examiner

*Primary Examiner*—Hezron Williams
*Assistant Examiner*—Alex Devito
(74) *Attorney, Agent, or Firm*—Henry M. Feiereisen; Ursula B. Day

(57) ABSTRACT

A pipe testing apparatus includes a rupture device for testing a rupture strength of a pipe. The rupture device has two clamping heads respectively accepting associated ends of the pipe which extends between the clamping heads, and a pressure-application system having a feed channel for imposing a fluid upon the pipe. The rupture device includes a tie rod which connects the clamping heads and extends through the pipe in coaxial relationship thereto such that an annular space is formed between the tie rod and the pipe, with the feed channel feeding into the annular space.

14 Claims, 3 Drawing Sheets

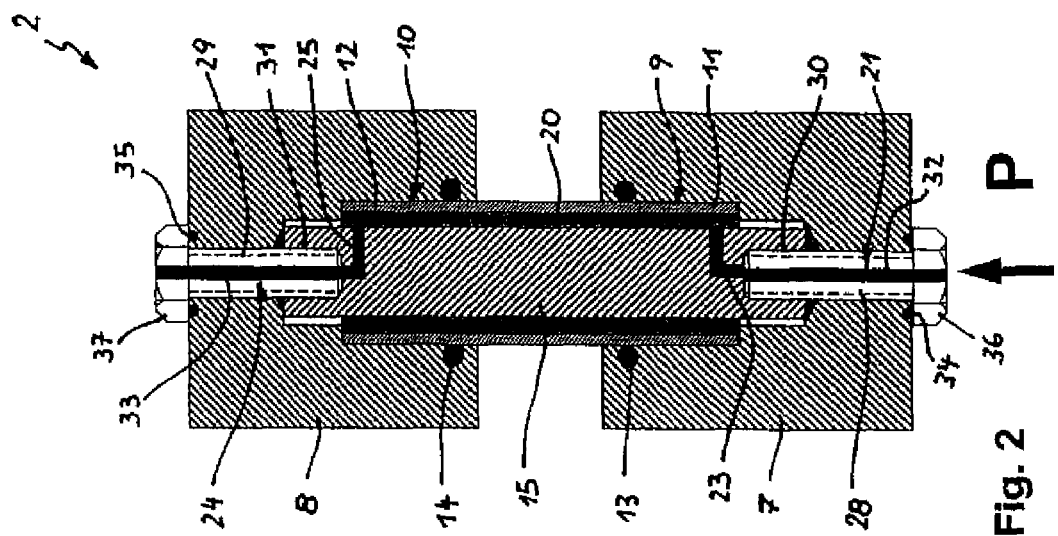
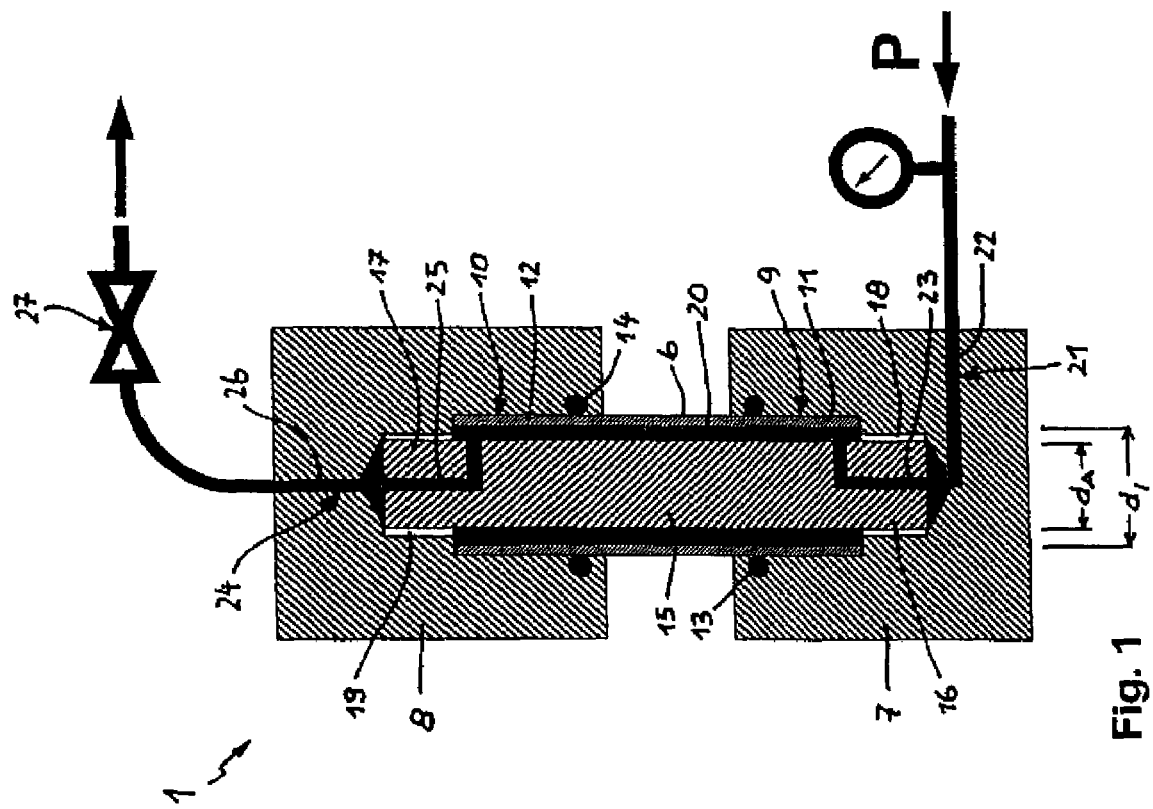

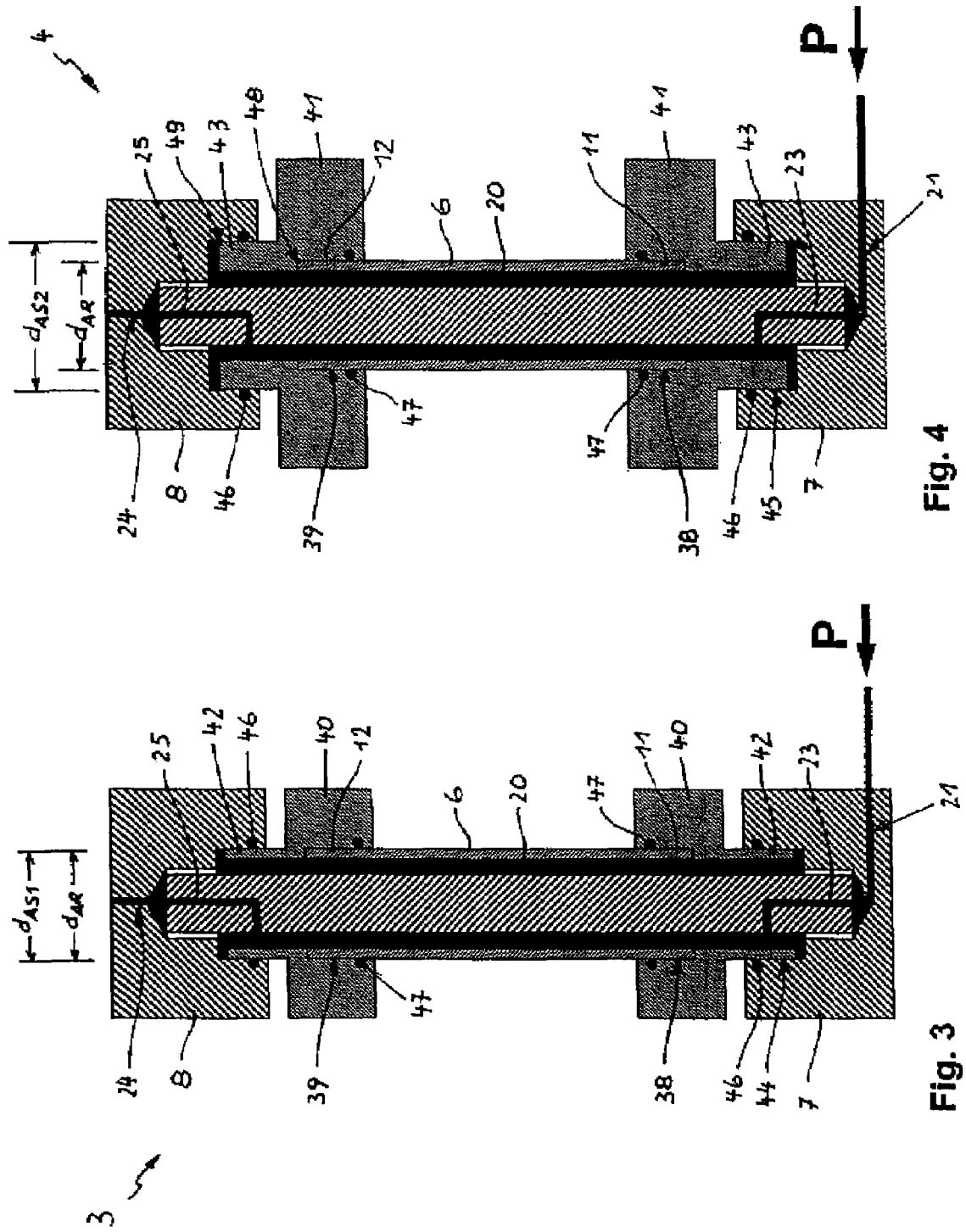

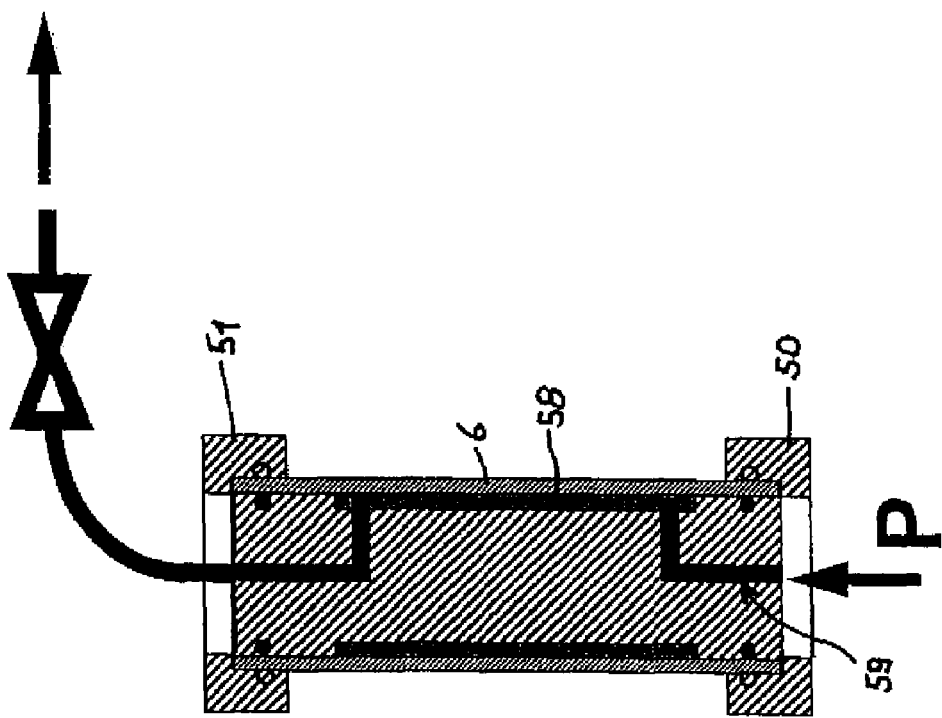
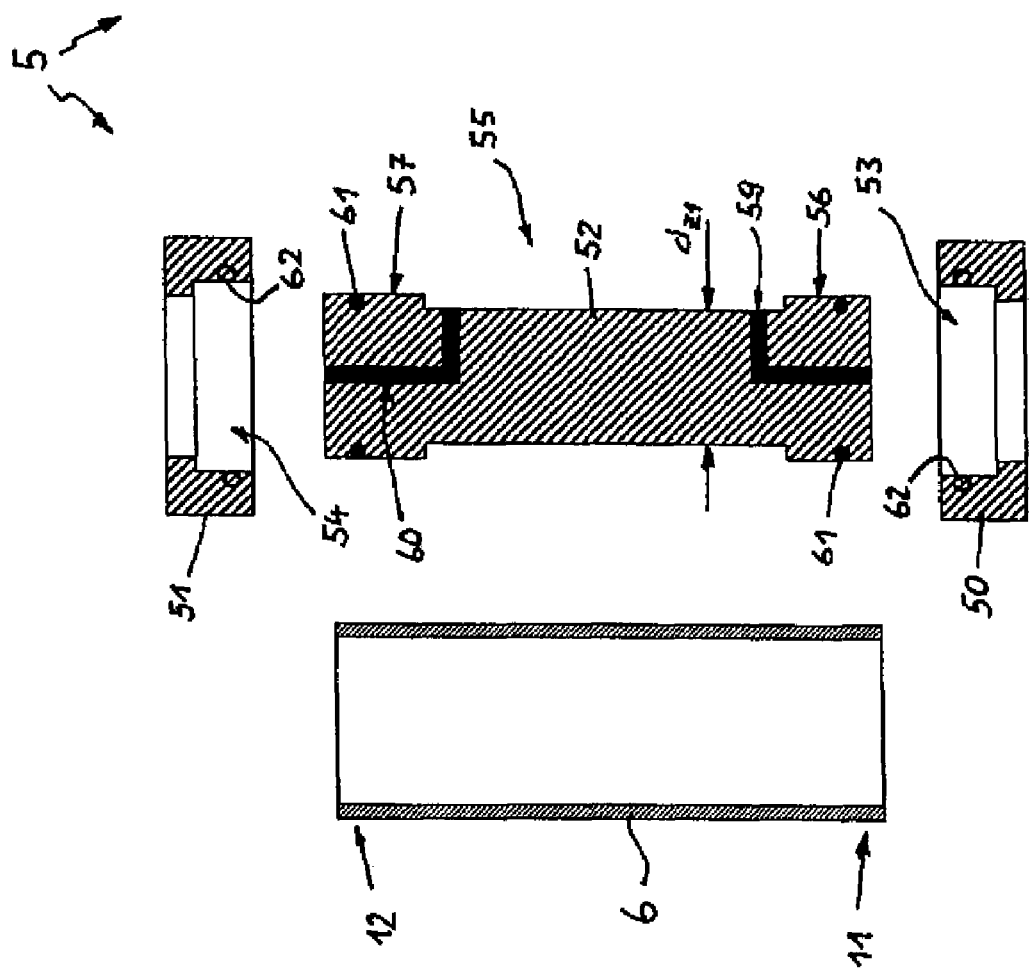
Fig. 5a
Fig. 5b

APPARATUS FOR TESTING A RUPTURE STRENGTH OF A PIPE

CROSS-REFERENCES TO RELATED APPLICATIONS

This application claims the priority of German Patent Application, Serial No. 10 2006 001 425.1, filed Jan. 10, 2006, pursuant to 35 U.S.C. 119(a)-(d), the content of which is incorporated herein by reference in its entirety as if fully set forth herein.

BACKGROUND OF THE INVENTION

The present invention relates to an apparatus for testing a rupture strength of a pipe.

Nothing in the following discussion of the state of the art is to be construed as an admission of prior art.

Pipes are subjected to stress-rupture tests in order to examine their rupture strength and/or to examine their material properties. These tests are carried out by a rupture device which closes the ends of a pipe being tested by means of clamping heads which are each associated to a traverse bar. Both traverse bars are interconnected by at least two anchoring rods. Once the interior space is filled with fluid, a pump subjects the pipe to a pressure force which is increased until the pipe is caused to rupture. As a result of the test, circumferential stress, fracture surface formation and the like can be evaluated.

It is known to provide a rupture device with clamping heads made of two parts. Each clamping head has a ram with cone and a conical shoe as abutment. The ram is inserted with the cone in one end of a pipe, whereby the end is widened in a funnel-shaped manner. Ram and conical shoes are clamped together to generate the necessary sealing forces, using bolts or hydraulic cylinders. Axial forces generated by the internal pressure are opposed by struts. This type of rupture device is complicated in structure and difficult to use.

It would therefore be desirable and advantageous to provide an improved pipe testing apparatus which obviates prior art shortcomings and is simple in structure while still being reliable in operation.

SUMMARY OF THE INVENTION

According to one aspect of the present invention, a pipe testing apparatus includes a rupture device for testing a rupture strength of a pipe, with the rupture device including two clamping heads respectively accepting associated ends of the pipe extending between the clamping heads, and a pressure-application system having a feed channel for imposing a fluid upon the pipe, wherein the rupture device includes a tie rod connecting the clamping heads and extending through the pipe in coaxial relationship thereto such that an annular space is formed between the tie rod and the pipe, with the feed channel feeding into the annular space.

The present invention resolves prior art problems by connecting the clamping heads with a tie rod which extends coaxially inside the pipe at a distance thereto so that an annular space is formed between the tie rod and the surrounding pipe and fluidly communicates with the feed channel. As a result, the rupture device can be constructed in a simple manner and with a reduced number of components. Forces caused by internal pressure buildup can now be absorbed by the internally disposed tie rod. There is no longer any need to widen the ends of the pipe being tested in order to form a sealing cone.

According to another feature of the present invention, the tie rod and the clamping heads can be bolted together. As a result, a stable linkage between tie rod and clamping heads is realized. In addition, the clamping heads are prevented by the tie rod from being pushed apart when the rupture device is activated to apply a pressure force upon the pipe. The pressure fluid is hereby introduced into the annular space via the feed channel in one of the clamping heads, whereby at least one channel section of the feed channel may extend through the tie rod.

According to another feature of the present invention, the pressure-application system has a vent channel which is connected to the annular space during an initial phase of the test so as to allow a ventilation of the annular space, when pressure fluid is introduced into the annular space.

According to another feature of the present invention, the clamping heads may each have a receptacle for direct acceptance of the associated ends of the tie rods. As an alternative, the rupture device may have adapters which are axially movably received in the clamping heads, respectively, with each adapter having a receptacle for respectively holding the ends of the tie rods. In this way, the presence of radial forces between the ends of the pipe and the clamping heads can be eliminated.

According to another feature of the present invention, the adapters may each have a necking for support in a pocket of the associated clamping head. The necking may hereby have an outer diameter which corresponds to an outer diameter of the pipe. As a result, the ends of the pipe are able to rest against the receptacles of the adapters when pressure is applied, and the pipe together with the adapters are able to freely contract axially, without the adverse effect of friction forces.

In order to simultaneously apply axial forces from the ends upon the pipe during the stress-rupture test, the outer diameter of the necking may be dimensioned greater than the outer diameter of the pipe. As a result, an axial force can be applied upon the pipe being tested during pressure application across larger surface areas between the necking and the clamping head.

The tie rod may have a constant outer diameter which can be slightly smaller than the inner diameter of the pipe being tested in order to form the annular space between the pipe and the tie rod. As an alternative, it is, of course, also conceivable to construct the tie bar longitudinally with plural length sections which have different diameters. Suitably, the tie rod has an end with an outer diameter which corresponds to the inner diameter of the pipe. In a central length section between the tie rod ends, the outer diameter is slightly smaller so that the annular space between tie rod and pipe is formed. Seals can be incorporated in the tie rod ends.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 1 is a schematic sectional view of a first embodiment of a pipe testing apparatus according to the present invention;

FIG. 2 is a schematic sectional view of a second embodiment of a pipe testing apparatus according to the present invention;

FIG. 3 is a schematic sectional view of a third embodiment of a pipe testing apparatus according to the present invention;

FIG. 4 is a schematic sectional view of a fourth embodiment of a pipe testing apparatus according to the present invention;

FIG. 5a is a schematic sectional exploded view of a fifth embodiment of a pipe testing apparatus according to the present invention; and FIG. 5b is a schematic sectional view of the pipe testing apparatus of FIG. 5a in assembled state.

DETAILED DESCRIPTION OF PREFERRED EMBODIMENTS

Throughout all the Figures, same or corresponding elements are generally indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic sectional view of a first embodiment of a pipe testing apparatus according to the present invention, generally designated by reference numeral 1, for carrying out a stress-rupture test. The rupture device 1 includes a lower clamping head 7 with a cylindrical receptacle 9 for sealingly accepting one end 11 of a pipe 6, and an upper clamping head 8 with a cylindrical receptacle 10 for sealingly accepting another end 12 of the pipe 6, Seals 13, 14 are disposed in the receptacles 9, 10 to provide a sealing between the receptacles 9, 10 and the ends 11, 12 of the pipe 6.

The clamping heads 7, 8 are connected by a central tie rod 15 which extends through the pipe 6 in coaxial relationship thereto. The tie rod 15 has opposite threaded ends 16, 17 which are secured in threaded sockets 18, 19 of the lower and upper clamping heads 7, 8, respectively. The threaded sockets 18, 19 are provided in the clamping heads 7, 8 below and above of the receptacles 9, 10, respectively, as viewed in the drawing plane.

The tie rod 15 has an outer diameter $d_A$ which is slightly smaller than an inner diameter $d_I$ of the pipe 6 so that an annular space 20 is formed between the tie rod 15 and the pipe 6. Feeding into the annular space 20 is a feed channel 21 for conducting a fluid supplied from a pressure source P. The feed channel 21 has a first channel section 22, which extends in the lower clamping head 7, and a second channel section 23, which extends through the tie rod 15. The annular space 20 is further connected to a vent channel 24 which has a channel section 25 extending through the tie rod 15 and a channel section 26 extending through the upper clamping head 8. A valve 27 opens or closes the vent channel 24.

The rupture device 1 for performing a stress-rupture test operates as follows: In a preliminary assembly phase, the lower threaded end 16 of the tie rod 15 is screwed into the socket 18 of the lower clamping head 7. Subsequently, the pipe 6 is placed over the tie rod 15 and the lower end 11 of the pipe 6 is positioned in the receptacle 9 of the lower clamping head 7. Next, the upper clamping head 8 with its receptacle 10 is attached to the upper end 12 of the pipe 6, and the tie rod 15 with its upper threaded end 17 is screwed into the socket 19 of the upper clamping head 8. The seals 13, 14 in the receptacles 9, 10 seal the annular space 20 against the outside.

Once the pipe 6 is positioned and the rupture device 1 is assembled, the system is flooded with fluid (active medium) via the feed channel 21. Valve 27 is hereby opened to allow escape of air trapped in the annular space 20 via the vent channel 24. The fluid flows essentially under no pressure from below upwards into the annular space 20. When the system is vented and filled with fluid, valve 27 is closed and the actual rupture test can commence. Pressure is imposed on the rupture device 1 by the pressure source P via the feed channel 21 until the pipe 6 ruptures. The tie rod 15 prevents hereby the lower and upper clamping heads 7, 8 from being pushed apart in longitudinal direction during pressure application.

Although not shown in detail for the sake of simplicity, the rupture device 1 includes measuring sensors, measuring devices and evaluation units in order to log, evaluate and document the test results.

Of course, the filling of the rupture device 1 and the pressure application may basically also be carried out in opposite direction. In other words, the vent channel 24 may be the feed channel and the feed channel 21 may be the vent channel.

After conclusion of the rupture test, the rupture device 1 is dismantled. This can be realized by simply removing the upper clamping head 8 and withdrawing the pipe 6 from the rupture device 1.

Referring now to FIG. 2, there is shown a schematic sectional view of a second embodiment of a pipe testing apparatus according to the present invention, generally designated by reference numeral 2. Parts corresponding with those in FIG. 1 are denoted by identical reference numerals and not explained again. The description below will center on the differences between the embodiments. In this embodiment, provision is made for tension bolts 28, 29 in order to secure the tie rod 15 in the lower and upper clamping heads 7, 8. The tension bolts 28, 29 extend in longitudinal direction of the tie rod 15 through the clamping heads 7, 8 and are screwed into threaded bores 30, 31 of the tie rod 15.

The feed channel 21 has a channel section 32, which extends through the tension bolt 28, and the vent channel 24 has a channel section 33, which extends through the tension bolt 29. Also in this embodiment, the feed channel 21 has a channel section 23 and the vent channel 24 has a channel section 25, with both channel sections 23, 24 routed through the tie bar 15. End seals 34, 35 seal the bolt heads 36, 37 of the tension bolts 28, 29 against the lower and upper clamping heads 7, 8.

The rupture device 2 executes the rupture test in an analogous manner as afore-described with reference to the rupture device 1 of FIG. 1.

Referring now to FIG. 3, there is shown a schematic sectional view of a third embodiment of a pipe testing apparatus according to the present invention, generally designated by reference numeral 3. Parts corresponding with those in FIG. 1 are denoted by identical reference numerals and not explained again. The description below will center on the differences between the embodiments. In this embodiment, the ends 11, 12 of the pipe 6 are received in receptacles 38, 39 which are formed in adapters 40, 41, respectively. The adapter 40 is hereby axially movably mounted in the clamping head 7, whereas the adapter 41 is axially movably mounted in the clamping head 8. The adapter 40 has a necking 42 which is supported in a pocket 44 of the lower clamping head 7, and the adapter 41 has a necking 43 which is supported in a pocket 45 of the upper clamping head 8. Seals 46, 47 are placed between the sockets 44, 45 and the neckings 42, 43 as well as between the pipe 6 and the receptacles 38, 39 in the adapters 40, 41, respectively.

When the pipe 6 undergoes a rupture test and is exposed to a pressure force, the pipe 6 is able to freely axially contract together with the adapters 40, 41. As a result of the mounting of the pipe 6 in the receptacles 38, 39 of the adapters 40, 41 and the floating support of the adapters 40, 41 in the clamping heads 7, 8, the presence of friction forces in a contact area between the receptacles 38, 39 and the ends 11, 12 of the pipe 6 is prevented, which friction forces could otherwise adversely affect the measurement and the test evaluation.

The outer diameter $d_{AS1}$ of the necking 42 corresponds to the outer diameter $d_{AR}$ of the pipe 6. This ensures that the ends 11, 12 of the pipe 6 rest against the cylinder surface of the receptacles 38, 39 during pressure application. The pipe 6 can be freely axially contract together with the adapters 40, 41 during pressure application.

Referring now to FIG. 4, there is shown a schematic sectional view of a fourth embodiment of a pipe testing apparatus according to the present invention, generally designated by reference numeral 4. Parts corresponding with those in FIG. 3 are denoted by identical reference numerals and not explained again. The description below will center on the differences between the embodiments. In this embodiment, the outer diameter $d_{AS2}$ of the necking 43 is greater than the outer diameter $d_{AR}$ of the pipe 6. During pressure application, an axial force is exerted upon the pipe 6 across an end surface 49 of the necking 43 which is greater than the end surface 48 of the pipe. In this way, the rupture test can be carried out with simultaneous introduction of axial forces into the pipe 6.

FIGS. 5a and 5b show schematic sectional views of a fifth embodiment of a pipe testing apparatus according to the present invention, generally designated by reference numeral 5. FIG. 5a shows hereby an exploded view of the rupture device 5, whereas FIG. 5b shows the assembled rupture device 5. The rupture device 5 includes a lower clamping head 50, an upper clamping head 51, and a tie rod 52 which interconnects the clamping heads 50, 51 and is securable in the clamping heads 50, 51. Formed in the clamping heads 50, 51 are receptacles 53, 54 for holding the ends 11, 12 of a pipe 6, respectively. The pipe 6 is positioned over the tie rod 52 so that the tie rod 52 extends coaxially through the pipe 6.

The tie rod 52 has a central rod section 55 of reduced diameter $d_{Z1}$ in comparison to its end portions 56, 57, as best seen in FIG. 5a. As a result, an annular space 58 is formed between the tie rod 52 and the pipe 6, when the rupture device 5 is assembled and ready for performing the rupture test. Feed channel 59 feeds into the annular space 58. In addition, the annular space 58 is connected to a vent channel 60. Seals 61 are disposed between the end portions 55, 56 of the tie rod 52 and the pipe 6 for effectively sealing the rupture device 5. As best seen in FIG. 5a, a spring element 62 is integrated in the receptacles 53, 54 to keep the ends 11, 12 of the pipe 6 in the clamping heads 50, 51.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein.

What is claimed is:

1. A pipe testing apparatus, comprising:
   a rupture device for testing a rupture strength of a pipe, said rupture device including two clamping heads respectively accepting opposite ends of the pipe extending between the clamping heads; and
   a pressure-application system having a feed channel for imposing a fluid upon the pipe,
   wherein the rupture device includes a tie rod connecting the clamping heads and extending through the pipe in coaxial relationship thereto such that an annular space is formed between the tie rod and the pipe, with the feed channel feeding into the annular space,
   wherein the rupture device has an adapter floatingly supported for axial movement in one of the clamping heads, said adapter having a receptacle for holding one end of the tie rod and a necking supported in a pocket of the one clamping head.

2. The pipe testing apparatus of claim 1, wherein the feed channel has a channel section extending through the tie rod.

3. The pipe testing apparatus of claim 1, wherein the pressure-application system has a vent channel connected to the annular space.

4. The pipe testing apparatus of claim 1, wherein the rupture device has another adapter floatingly supported for axial movement in the other one of the clamping heads and having a receptacle for holding the other end of the tie rod.

5. The pipe testing apparatus of claim 4, wherein the other adapter has a necking supported in a pocket of the other clamping head.

6. The pipe testing apparatus of claim 1, wherein the necking has an outer diameter which corresponds to an outer diameter of the pipe.

7. The pipe testing apparatus of claim 1, wherein the necking has an outer diameter which is greater than an outer diameter of the pipe.

8. The pipe testing apparatus of claim 1, wherein the tie bar is formed longitudinally with plural length sections which have different diameters.

9. The pipe testing apparatus of claim 8, wherein a central length section of the tie bar has an outer diameter of reduced size to form the annular space.

10. The pipe testing apparatus of claim 1, wherein the feed channel is formed in one of the clamping heads, and the vent channel is formed in the other one of the clamping heads.

11. The pipe testing apparatus of claim 1, wherein the tie rod has a constant outer diameter which is slightly smaller than an inner diameter of the pipe to form the annular space between the pipe and the tie rod.

12. The pipe testing apparatus of claim 1, wherein the tie rod has an end defined by an outer diameter which corresponds to the inner diameter of the pipe.

13. The pipe testing apparatus of claim 1, further comprising seals for placement in ends of the tie rod.

14. The pipe testing apparatus of claim 1, further comprising a spring element received in a sidewall of each of the receptacles for keeping the ends of the pipe in the clamping heads.

* * * * *